(12) United States Patent
Wood et al.

(10) Patent No.: US 6,514,951 B1
(45) Date of Patent: Feb. 4, 2003

(54) POUR-ON FORMULATIONS EFFECTIVE FOR THE CONTROL OF INTERNAL AND EXTERNAL PARASITES OF HOMOTHERMIC ANIMALS

(75) Inventors: Irwin B. Wood, Yardley, PA (US); James Quinlan, Trenton, NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 08/087,548

(22) Filed: Jul. 6, 1993

Related U.S. Application Data

(63) Continuation-in-part of application No. 07/800,347, filed on Nov. 27, 1991, now abandoned, which is a continuation-in-part of application No. 07/661,768, filed on Feb. 27, 1991, now abandoned, which is a continuation-in-part of application No. 07/451,472, filed on Dec. 15, 1989, now abandoned.

(51) Int. Cl.$^7$ .................. A61K 31/695; A61K 31/24
(52) U.S. Cl. .............................. 514/63; 514/539
(58) Field of Search ..................... 514/63, 539

(56) References Cited

U.S. PATENT DOCUMENTS

| | | | |
|---|---|---|---|
| 4,607,050 A | 8/1986 | Kieran et al. | 514/520 |
| 4,859,657 A | 8/1989 | O'Sullivan et al. | 514/63 |
| 4,871,719 A | 10/1989 | Maienfisch | 514/63 |
| 4,916,154 A | 4/1990 | Sato et al. | 514/450 |
| 4,925,671 A * | 5/1990 | Abber | 424/448 |

FOREIGN PATENT DOCUMENTS

| | | | |
|---|---|---|---|
| AU | 31278/84 | 2/1985 | |
| AU | 11221/88 | 4/1989 | |
| EP | 0120286 | 10/1984 | A01N/25/02 |
| EP | 0136033 | 4/1985 | |
| EP | 0241145 | 10/1987 | |
| EP | 0254583 | 1/1988 | |
| EP | 0259779 | 3/1988 | |
| EP | 0311180 | 4/1989 | |
| EP | 0329460 | 8/1989 | A61K/31/71 |
| GB | 2094626 | 9/1982 | A01N/25/02 |

OTHER PUBLICATIONS

S. Parker, "Dictionary of Scientific and Technical Terms," 4th Ed., 1989, pp. 1023, 1212, McGraw–Hill Book Co., N.Y. Chemical Abstracts, vol. 111, No. 17, Oct. 23, 1989, p. 270, Abstr. No. 148925m & JP–01025706 (1/89).

* cited by examiner

*Primary Examiner*—Russell Travers
(74) *Attorney, Agent, or Firm*—Joseph M. Mazzarese

(57) ABSTRACT

There are provided non-aqueous pour-on, water-fast formulations effective for the control of internal and external parasitic infections and infestations of homothermic animals such as mammalian quadrupeds. The pour-on formulations of the present invention contain as the active ingredient, a compound selected from the group consisting of LL-F28249α-λ, 23-oxo (keto) and 23-imino derivatives of the compounds collectively defined as LL-F28249, and milbemycin and avermectin molecules.

13 Claims, No Drawings

POUR-ON FORMULATIONS EFFECTIVE FOR THE CONTROL OF INTERNAL AND EXTERNAL PARASITES OF HOMOTHERMIC ANIMALS

This is a continuation-in-part of U.S. application Ser. No. 07/800,347 filed on Nov. 27, 1991 now abandoned, which is a continuation-in-part of U.S. application Ser. No. 07/661,768 filed on Feb. 27, 1991, now abandoned, which in turn is a continuation-in-part of U.S. application Ser. No. 07/451,472 filed on Dec. 15, 1989, abandoned.

BACKGROUND OF THE INVENTION

Pour-on formulations are utilized by the animal industry as a means for administering certain anthelmintic agents and veterinary medicines to animals. In practice, the medicated formulation is applied directly to the external skin or hide of the animal. As such, some practitioners have extended the term pour-on to include formulations which may be dispersed in water and applied as aqueous dips, baths or sprays. In the present specification, however, the term "pour-on" is not intended to suggest this type of application. Rather, the formulation of this invention is a non-aqueous formulation which is applied with the assistance of a suitable device such as a measuring cup, a squirt bottle or an automatic microspray device which permits directed application of a small amount of formulation onto the skin of the animal being treated.

While a number of anthelmintic agents and veterinary medicines such as tetramisole, levamisole, trichlorphon and fenthion, have been successfully prepared as pour-on compositions, all veterinary medicines do not lend themselves to such formulation. Moreover, those medicines that have been so formulated generally have been found to be significantly less effective as pour-on formulations than they are when administered orally or parenterally.

Presently, the art appears to describe no pour-on formulations which do not wash off during rainfall or which retain efficacy on wet animals. From a practical standpoint, a product which lacks efficacy on wet skin or hide is extremely inconvenient to use due to the extra burden on the part of the farmer to keep the animals dry in order to effectively treat them with pour-on medicine.

For successful formulation as a pour-on, a drug must be active when dissolved, dispersed or emulsified in a suitable solvent which is well tolerated by the animals skin. The drug must be readily adsorbable through the animals skin and the composition as a whole should disperse or spread well over the animals body and be relatively non-viscous when so spread. It must also be recognized that each drug has its own chemical and physical properties that require special consideration and limit the types of solvents, diluents, stabilizing agents and other formulatory agents that can be employed in the formulation of that particular drug or medicine.

It is, therefore, an object of the present invention to provide a non-irritating pour-on formulation which is effective on dry or wet skin and hide for the control of insects and internal and external parasitic infections and infestations of farm and companion animals and which resists wash off during normal precipitation.

It is also an object of this invention to provide an effective non-aqueous pour-on formulation that contains, as the active ingredient, an antibiotic selected from LL-F28249α, a 23-oxo or 23-imino derivative of LL-F28249α-λ, a milbemycin molecule or an avermectin molecule, which exhibits excellent penetration of the animals hide or skin, spreads well and rapidly over the animals body, is non-malodorous, non-irritating and relatively non-viscous toward dust, dirt and foreign matter encountered by the treated animals.

It is a further object of this invention to provide a method for treating, controlling, preventing or protecting quadruped farm and companion animals from infestation and infection by helminths, acarids and arthropod endo- and ectoparasitic insects by topically applying to said animals a pour-on formulation containing an anthelmintically, acaricidally or arthropod endo- or ectoparasiticidally effective amount of the antibiotic LL-F28249α, LL-F28249β or a 23-oxo or 23-imino derivative of LL-F28249α, such as 23-(O-methyloxime)-LL-F28249α or 23-(O-methyloxime)-LL-F28249β.

SUMMARY OF THE INVENTION

The present invention relates to non-aqueous pour-on, water-fast compositions and the method of use thereof for treating, controlling, preventing and protecting homothermic animals, such as mammalian quadrupeds, from infestation and infection by internal and external parasites. More particularly, this invention relates to non-aqueous pour-on compositions containing as the active ingredient an anthelmintically, acaricidally or arthropod endo- or ectoparasiticidally effective amount of a compound selected from compounds designated LL-F28249α-λ, a 23-oxo or 23-imino derivative of LL-F28249α-λ, a milbemycin molecule or an avermectin molecule.

DESCRIPTION OF THE PREFERRED EMBODIMENTS

The compounds designated LL-F28249α-λ are (collectively) isolates from the fermentation broth of the microorganism *Streptomyces cyaneogriseus* subspecies *noncyanogenus,* deposited in the NRRL under deposit accession No. 15773. The method for preparation of the LL-F28249 compounds is disclosed in U.S. Pat. No. 5,106,994 and is incorporated herein by reference thereto.

The 23-oxo (keto) and 23-imino derivatives of LL-F28249α-λ compounds, useful in the pour-on formulations of this invention, are disclosed in U.S. Pat. No. 4,916,154, incorporated herein by reference thereto. Although U.S. Pat. No. 4,916,154 indicates that the 23-oxo (keto) and 23-imino derivatives of LL-F28249α-λ may be administered by pouring on the skin of an animal via a solution, it only suggests that the active compound may be dissolved in dimethylsulfoxide, propylene glycol or the like or in a combination of solvents. These formulations are not entirely satisfactory since the use of dimethylsulfoxide can cause instability of the 23-(oxo) or 23-imino derivatives of LL-F28249α-λ and/or leave a malodorous scent on the treated animal. The propylene glycol compositions tend to be sticky and collect dust and dirt and debris from the animals' surroundings.

The pour-on veterinary compositions of this invention have the following formulations:

|     | % w/v     | Compound          |
| --- | --------- | ----------------- |
| (A) | 0.1–5.0   | Active ingredient |
|     | 5.0–20.0  | Aromatic solvent  |

-continued

| | % w/v | Compound |
|---|---|---|
| | 2.0–15.0 | PPG-2 Myristyl ether propionate (spreader) |
| | 0–15.0 | Polybutene (number average molecular weight range from 320 to 3000) |
| | QS to 100% | Mineral or vegetable oil; or |
| (B) | 0.1–5.0 | Active ingredient |
| | 0–15.0 | Polysorbate 80 |
| | QS to 100% | Butoxyethoxyethanol |

These compositions may be prepared by dissolving, dispersing or emulsifying about 0.1% to 5.0% w/v of the active ingredient, i.e. a compound selected from the group consisting of LL-F28249α-λ, a 23-oxo or 23-imino derivative of said compound LL-F28249α-λ, a milbemycin molecule or an avermectin molecule, in a mixture consisting essentially of 5.0% to 20.0% w/v of an aromatic solvent having a Kauri-butanol value between about 90 to about 96, a mixed aniline point between about 13.4° C. to about 15.4° C. and a specific gravity @ 15.6°/15.6° C. of about 0.872 to about 0.985; about 1.0% to about 15.0% w/v of PPG-2 myristyl ether propionate; if present, about 1.0% w/v to about 15.0% w/v of a polybutene having a number average molecular weight range of 320 to 3000; and the remainder of the mixture a pharmacologically acceptable oil such as mineral or vegetable oil. Pour-on formulations prepared as described above with LL-F28249α, LL-F28249β, 23-(O-methyloxime)-LL-F28249α or 23-(O-methyloxime)-LL-F28249β, are especially effective for controlling endo- and ectoparasites on mammalian quadrupeds.

The pour-on compositions of the invention may also be prepared by dissolving, dispersing or emulsifying about 0.1% to 5.0% w/v of a compound selected from the group consisting of LL-F28249α-λ, a 23-oxo or 23-imino derivative of said antibiotic LL-F28249α-λ, a milbemycin molecule and an avermectin molecule, in butoxyethoxyethanol. Pour-on formulations prepared as described above with LL-F28249α, LL-F28249β, 23-(O-methyloxime)-LL-F28249α or 23-(O-methyloxime)-LL-F28249β, are especially effective for controlling endo- and ecto-parasites on mammalian quadrupeds. The admixture of up to about 15.0% w/v of polysorbate 80 with the above composition is optional.

Excipients such as dyes, antimicrobial agents, antioxidants or mixtures thereof may be included in the compositions of the invention. The amounts of said excipients suitable for use in the invention range from about 0.005% to 2.0% on a weight/volume basis.

Dyes suitable for use in the present invention include anthraquinone dyes, azo dyes and the like. Examples of antimicrobial agents useful in the compositions of the present invention are benzoic acid derivatives, methylparaben, propylparaben and the like. And antioxidants suitable for use in the compositions of the invention include butylated hydroxytoluene, butylated hydroxyanisoles, tertiarybutylhydroxyquinolone, sodium bisulfite, sodium metabisulfite, propyl gallate and the like and mixtures thereof.

Advantageously, the compositions of the present invention are well tolerated by the animals and non-damaging to the animals' skin, hide or hair. The formulations are non-malodorous. They spread well and rapidly over the animal's body and the active ingredient thereof is found to be readily absorbed through the hide or skin of the treated animals. A further benefit is that the compositions retain efficacy on wet skin or hide of the animal and resist wash off during precipitation such as rain. The term "water-fast" used herein is intended to mean that the compositions resist being washed off in typical wet weather such as rainfall, snowfall, etc.

The preferred active ingredients useful in the preparation of the compositions of this invention have the following structures:

23-(O-methyloxime)-LL-F28249α

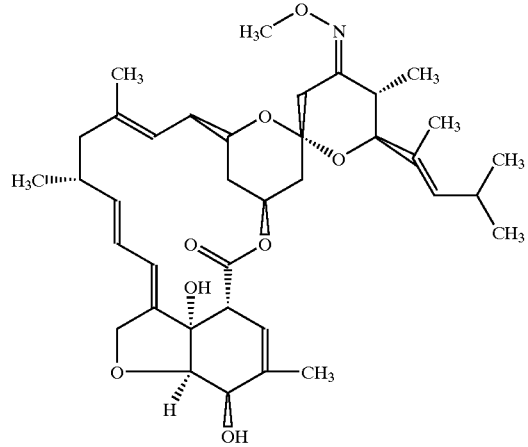

and

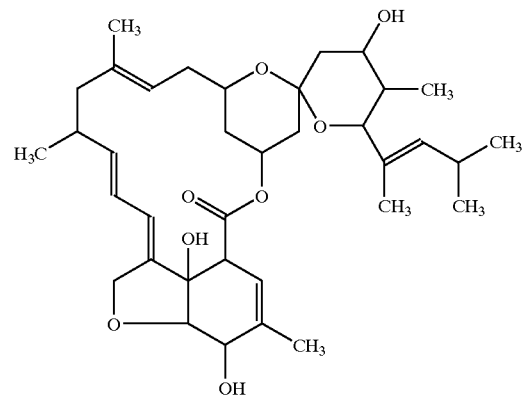

The compositions of this invention are highly effective for protecting or treating farm and companion animals, particularly mammalian quadrupeds such as cattle, sheep, deer, horses, swine, goats, dogs, cats and the like, against infection and infestation by helminths, nematodes, acarids and arthropod endo- and ectoparasitic insects.

Helminthiases is a widespread disease found in many farm and companion animals and responsible for significant economic losses throughout the world. Among the helminths most frequently encountered are the group of worms referred to as nematodes. The nematodes are found in the intestinal tract, heart, lungs, blood vessels and other body tissues of animals and are a primary cause of anemia, weight loss and malnutrition in the infected animals. They do serious damage to the walls of the gastrointestinal tract and the tissue of the organs in which they reside and, if left untreated, may result in death to the infected animals.

The nematodes most commonly found to be the infecting agents of animals include Haemonchus and Ostertagia generally found in the stomach; Cooperia, Oesphagostomum and Nematodirus generally found in the intestinal tract and Dictyocaulus found in the lungs. Treatment of animals to prevent infestation thereof by the above nematodes or to reduce or control the proliferation of these infecting agents in animals is thus an important and desirable advantage of the present invention.

Besides controlling helminths and nematodes, the present invention also controls several arthropod endo- parasitic infestations such as cattle grub infestations.

It has been further found that acarid and arthropod ectoparasitic insect infestations may be controlled, prevented or eliminated by applying to said animals an acaricidally or ectoparasiticidally effective amount of the above-described LL-F28249 compound or derivative thereof or milbemycin or avermectin molecule. This can be achieved by applying the active compound to the skin, hide and/or hair of the animals, usually in the form of a liquid formulated composition in sufficient amount to provide the treated animal with about 0.1 mg to 5.0 mg of active compound per kg of animal body weight. In practice it is found that generally 0.2 mg to 2.0 mg of LL-F28249α, LL-F28249β, 23-(O-methyloxime)-LL-F28249α or 23-(O-methyloxime)-LL-F28249β, is sufficient to control helminths such as *Ostertagia circumcincta, Haemonchus contortus* and *Trichostrongylus colubriformis*.

It has also been found that the pour-on composition disclosed in this application, which contains 23-(O-methyloxime)-LL-F28249α as the active ingredient, provides excellent control of the biting louse, *Damalinia ovis* and *Damalinia bovis*. Moreover, it has been found that this formulation which contains 23-(O-methyloxime)-LL-F28249α is unique in its ability to provide superior control of *Psoroptes ovis* which cause psoroptic mange on animals, such as cattle and sheep. This active ingredient also finds beneficial use in treating or controlling chorioptic, sarcoptic and demodectic mange on an animal which has been caused by infestation of *Chorioptes bovis, Sarcoptes scabiei* and the Demodex species, respectively.

The present invention is further delineated by the examples set forth below which are provided simply by way of illustration and not intended to be limitations of the invention.

EXAMPLE 1

Evaluation of 23-(O-Methyloxime)-LL-F28249αfor Control of Psoroptic Mange, *Psoroptes ovis,* on Cattle The pour-on formulation of the present invention is prepared by blending together 0.5% w/v of 23-(O-methyloxime)-LL-F28249α; 10% w/v of an aromatic solvent having (1) a mixed aniline point of 15.4° C. (test method ASTM D 611), (2) Kauri-butanol value 92, (3) specific gravity @ 15.6°/15.6° C. of 0.899, (4) viscosity, CP @ 25° C. 1.20 and (5) a mass composition aromatic $C_9$-8% w/v, $C_{10}$-74%, $C_{11}$-15% and $C_{12}$-1%; 5% w/v of the emollient ester PPG-2 myristyl ether propionate, (spreader) melting point −5° C.; and 84.5% w/v of light mineral oil.

Calves with naturally acquired infestations of psoroptic mange are randomly selected weighed and tagged. The calves are then treated by pouring the test formulation down the midline of the back of test animals at volumes providing 10 ml of formulation per 100 kg of live animal body weight or 0.5 mg of active ingredient per kg live weight. The treated calves are placed in pens and provided feed and water ad libitum. The calves are inspected on days 7 and 14 after treatment for the presence of psoroptic mange live mites. Data obtained are reported below in Table 1.

TABLE 1

Evaluation of 23-(O-Methyloxime)-LL-F28249α Formulation for Controlling Psoroptic Mange on Cattle

| Treatment | Initial[2] Infestation | Live weight (kg) | Total Dose mL | Effect of Post-treatment | |
|---|---|---|---|---|---|
| | | | | Day 7 | Day 14 |
| 23-(O-methyloxime)-LL-F28249α pour-on formulation | +++ | 170 | 17 | mange at one site | no mites healthy skin[b] |
| 23-(O-methyloxime)-LL-F28249α pour-on formulation | ++ | 150 | 15 | two mites | no mites[b] healthy skin |
| 23-(O-methyloxime)-LL-F28249α pour-on formulation | ± | 170 | 17 | no mites | no mites[b] healthy skin |
| untreated control | *** | 150 | 0 | no change[c] | — |
| untreated control | ± | 160 | 0 | no change | no change |

[a]Assessment of aternal infestation
+++ = high
++ = moderate
± = very light
[b]Cured
[c]treated with commercial product to cure mange to save animal.

EXAMPLE 2

Preparation of Pour-On Formulations Containing 23-(O-Methyloxime)-LL-F28249α for Controlling Gastrointestinal Nematodes and the Biting Louse of Sheep Using the procedure of Example 1, the following formulations are prepared:

1)
(a) 0.5% w/v 23-(O-methyloxime)-LL-F28249α
(b) 10.0% w/v aromatic solvent sp. gravity @ 15.6°/15.6° C.=0.899, mixed aniline point 15.4° C. and Kauri-butanol value 92 (commercially available as AROMATIC® 150, Exxon Chemical Company, Houston, Tex.)
(c) 5.0% w/v PPG-2 myristyl ether propionate (spreader, commercially available as CRODAMOL® PMP, Croda, Inc., Parsippany, N.J.)
(d) 84.5% w/v light mineral oil 2)
- (a) 0.2% w/v 23-(O-methyloxime)-LL-F28249α
- (b) 10.0% w/v aromatic solvent sp. gravity @ 15.6°/15.6° C.=0.899, mixed aniline point 15.4° C. and Kauri-butanol value 92
- (c) 5.0% w/v PPG-2 myristyl ether propionate
- (d) 84.8% w/v light mineral oil 3)
- (a) 0.5% w/v 23-(O-methyloxime)-LL-F28249α
- (b) 10.0% w/v aromatic solvent sp. gravity @ 15.6°/15.6° C.=0.899, mixed aniline point 15.4° C. and Kauri-butanol value 92
- (c) 5.0% w/v PPG-2 myristyl ether propionate
- (d) 74.5% w/v light mineral oil
- (e) 10.0% w/v polybutene H-1900 kinematic viscosity at 99° C.=4069–4382 Flash point open cup=243° C. Specific gravity at 15.5° C.=0.898–0.916 Molecular weight number average=2300 (agent promoting adhesion and water repellency, commercially available as INDOPOL® H-1900, Amoco Chemical Co., Chicago, Ill.)

4)
- (a) 0.2% w/v 23-(O-methyloxime)-LL-F28249α
- (b) 10.0% w/v aromatic solvent sp. gravity @ 15.6°/15.6° C.=0.899, mixed aniline point 15.4° C. and Kauri-butanol value 92
- (c) 5.0% w/v PPG-2 myristyl ether propionate
- (d) 74.8% light mineral oil
- (e) 10.0% w/v polybutene H 1900 kinematic viscosity at 99° C.=4069–4382 Flash point open cup=243° C. Specific gravity at 15.5° C.=0.898–0.916 Molecular weight member average=2300

5)
- (a) 0.5% w/v 23-(O-methyloxime)-LL-F28249α
- (b) 99.5% w/v butoxyethoxyethanol 6)
- (a) 0.2% w/v 23-(O-methyloxime)-LL-F28249α
- (b) 99.8% w/v butoxyethoxyethanol 7)
- (a) 0.5% w/v 23-(O-methyloxime)-LL-F28249α
- (b) 10.0% w/v polysorbate 80, a nonionic surfactant-polyoxyethylene (20) sorbitan monooleate
- (c) 89.5% w/v butoxyethoxyethanol 8)
- (a) 0.2% w/v 23-(O-methyloxime)-LL-F28249α
- (b) 10.0% w/v polysorbate 80, a nonionic surfactant-polyoxyethylene (20) sorbitan monooleate
- (c) 89.8% w/v butoxyethoxyethanol 9)
- (a) 0.5% w/v 23-(O-methyloxime)-LL-F28249α
- (b) 15.0% w/v aromatic solvent sp. gravity @ 15.6°/15.6° C.=0.899, mixed aniline point 15.4° C. and Kauri-butanol value 92
- (c) 10.0% w/v PPG-2 myristyl ether propionate
- (d) 10.0% w/v polybutene having a molecular weight number average=2300
- (e) 0.05% w/v butylated hydroxyanisole (antioxidant)
- (f) 0.1% w/v D+C Violet #2 (dye)
- (g) 74.3% w/v mixed capric/caprylic glyceryl triester 10)
- (a) 0.5% w/v 23-(O-methyloxime)-LL-F28249α
- (b) 15.0% w/v aromatic solvent sp. gravity @ 15.6°/15.6° C.=0.872, mixed aniline point 13.4° C. and Kauri-butanol value 91 (commercially available as AROMATIC® 100, Exxon Chemical Company, Houston, Tex.)
- (c) 10.0% w/v PPG-2 myristyl ether propionate
- (d) 10.0% w/v polybutene having a molecular weight number average=2300
- (e) 0.05% w/v mixture of 20.0% w/w butylated hydroxyanisole, 6.0% w/w tert-butylhydroquinone, 4.0% w/w citric acid and 70.0% w/w propylene glycol (an antioxidant commercially available as TENOX®-22 from Eastman Chemical Company, Kingsport, Tenn.)
- (f) 0.025% w/v D+C Violet #2 (dye)
- (g) QS to 100% w/v mixed capric/caprylic glyceryl triester

EXAMPLE 3

Evaluation of Pour-On Formulations Containing 23-(O-Methyloxime)-LL-F28249α for Controlling Gastrointestinal Nematodes in Sheep Merino sheep are given artificially-induced infestations of *Damalinia ovis,* the biting louse, and artificially-induced infections of the gastrointestinal nematodes *Ostertagia circumcincta, Haemonchus contortus* and *Trichostrongylus colubriformis.* The sheep are then sheared, weighed and placed in individual pens. The infected sheep are then treated with the selected formulation by pouring the formulation down the midline of the sheeps' back. The formulations are then applied to the weighed sheep in sufficient amount to provide from 0.2 to 1.0 mg/kg of live animal body weight. Fourteen days after treatment, three sheep from each treatment and the control group are necropsied and the nematodes recovered and counted. Data obtained are reported in Table 2 below where it can be seen that the formulations prepared in Example 2 are highly effective against the abomasal nematodes *Ostertagia circumcincta* and *Haemonchus contortus* at doses of 0.2 mg/kg and 0.5 mg/kg or 1 mg/kg when poured along the midline on the backs of off-sheared sheep. It can also be seen that doses of from 0.5 mg/kg to 1 mg/kg of the 23-(O-methyloxime)-LL-F28249α provided in the above-said formulations are effective for controlling the intestinal bankrupt worm, *Trichostrongylus colubriformis.* In these tests nematode egg counts drop to nearly zero after treatment and remain that way to the end of the trial.

From Table 3 below, it can also be seen that the pour-on formulations are highly effective against the biting louse, *Damalinia ovis,* throughout the six week trial period.

TABLE 2

Efficacy of 23-(O-Methyloxime)-LL-F28249α Pour-On Against Nematodes in Sheep

| Formulation | Dose mg/kg | Dosage mL/10 kg | *Ostertagia circumcincta* | *Haemonchus contortus* | *Trichostrongylus colubriformis* |
|---|---|---|---|---|---|
| Control | 0 | 0 | 2025* | 428* | 1375* |
| | | | | % Efficacy | |
| 1 | 1.0 | 2 | 100 | 100 | 99.6 |
| 1 | 0.5 | 1 | 100 | 100 | 72 |

TABLE 2-continued

Efficacy of 23-(O-Methyloxime)-LL-F28249α Pour-On Against Nematodes in Sheep

| Formulation | Dose mg/kg | Dosage mL/10 kg | Ostertagia circumcincta | Haemonchus contortus | Trichostrongylus colubriformis |
|---|---|---|---|---|---|
| 2 | 0.2 | 1 | 96 | 89 | 24 |
| 3 | 1.0 | 2 | 100 | 100 | 89 |
| 3 | 0.5 | 1 | 100 | 100 | 76 |
| 4 | 0.2 | 1 | 100 | 100 | 17 |
| 5 | 1.0 | 2 | 100 | 100 | 47 |
| 5 | 0.5 | 1 | 99.7 | 100 | 31 |
| 6 | 0.2 | 1 | 92 | 81 | 17 |
| 7 | 1.0 | 2 | 100 | 100 | 64 |
| 7 | 0.5 | 1 | 99 | 100 | 7 |
| 8 | 0.2 | 1 | 93 | 81 | 60 |

*Arithmetic Mean Adult Worm Count, 14 days post-treatment
The worm egg counts of the remaining sheep are markedly reduced from the initial levels at the time of treatment at the end of the six-week trial period.

TABLE 3

Efficacy of 23-(O-Methyloxime)-LL-F28249α Pour-On Against the Biting Louse, *Damalinia ovis*, on Sheep

| Formulation | Dose mg/kg | Dosage mL/kg | 0 | 2 Weeks | 4 Weeks | 6 Weeks |
|---|---|---|---|---|---|---|
| Control | | | 16.3 | 10.3 | 8.7 | 8 |
| 1 | 1.0 | 2 | 46.3 | 0.67 | 0 | 0 |
| 1 | 0.5 | 1 | 30 | 1.3 | 0 | 0 |
| 2 | 0.2 | 1 | 35 | 3.3 | 1 | 1 |
| 3 | 1.0 | 2 | 27 | 0.33 | 0 | 0 |
| 3 | 0.5 | 1 | 21 | 0.67 | 0 | 0 |
| 4 | 0.2 | 1 | 18.7 | 10.3 | 4 | 1 |
| 5 | 1.0 | 2 | 57.3 | 0 | 0 | 0 |
| 5 | 0.5 | 1 | 36.7 | .5 | 0 | 0 |
| 6 | 0.2 | 1 | 32 | 1.3 | 1 | 0.7 |
| 7 | 1.0 | 2 | 16.3 | .67 | 0 | 0 |
| 7 | 0.5 | 1 | 40.0 | 1.0 | 0.67 | 0.67 |
| 8 | 0.2 | 1 | 44.0 | 0 | 3.3 | 5.7 |

Average No. of Lice column spans 0, 2 Weeks, 4 Weeks, 6 Weeks.

EXAMPLE 4

Evaluation of Formulations Containing 23-(O-Methyloxime)-LL-F28249α on Blood Serum Levels in Calves Treated with Pour-On Formulations Containing 23-(O-Methyloxime)-LL-F28249α

In these tests four calves per treatment are used to evaluate formulations 1 and 3 reported in Example 2, above. Cattle receiving formulation 1, from Example 2, are designated Group B, cattle receiving formulation 3 are designated Group C. The pour-on formulations are applied along the backs of the animal with 2 mL per kg of animal body weight of the test formulation to provide each animal with 1 mg/kg of 23-(O-methyloxime)-LL-F28259α in the selected formulation.

Blood samples are then taken from the treated animals at intervals up to 96 hours after treatment and the blood serum levels for the treated animals assayed.

From the data provided in Table 4 below, it can be seen that serum levels in calves receiving the CRODAMOL® formulation 1 (Group B) show an increase in blood levels to 11, 10 and 13.5 ppb at 48, 72 and 96 hours respectively, whereas, the CRODAMOL®-INDOPOL® formulation 3 Group C) shows enhanced blood levels to 8, 17.5 and 15.2 ppb at 48, 72 and 96 hours respectively. The higher blood levels are desirable.

TABLE 4

Evaluation of 23-(O-Methyloxime)-LL-F28249α Residues in Cattle Serum (ppb)
Formulation: 0.5% w/v 23-(O-methyloxime)-LL-F28249α Pour-On
Treatment Rate: 1 mg/kg body weight

| Group | Calf No. | 0 | 1 | 2 | 4 | 6 | 12 | 18 | 24 | 36 | 48 | 72 | 96 |
|---|---|---|---|---|---|---|---|---|---|---|---|---|---|
| B | 1 | <5 | <5 | <5 | <5 | <5 | 7 | 9 | 9 | 8 | 22 | 21 | 21 |
| B | 2 | <5 | <5 | <5 | <5 | <5 | <5 | 7 | 7 | 7 | 8 | 8 | 12 |

TABLE 4-continued

Evaluation of 23-(O-Methyloxime)-LL-F28249α Residues in Cattle Serum (ppb)
Formulation: 0.5% w/v 23-(O-methyloxime)-LL-F28249α Pour-On
Treatment Rate: 1 mg/kg body weight

| | | HOURS | | | | | | | | | | |
|---|---|---|---|---|---|---|---|---|---|---|---|---|
| Group | Calf No. | 0 | 1 | 2 | 4 | 6 | 12 | 18 | 24 | 36 | 48 | 72 | 96 |
| B | 3 | <5 | <5 | <5 | <5 | <5 | <5 | <5 | <5 | 6 | 5 | <5 | 11 |
| B | 4 | <5 | <5 | <5 | <5 | <5 | 6 | 7 | 7 | 8 | 8 | 7 | 10 |
| | Average | <5 | <5 | <5 | <5 | <5 | 5 | 7 | 7 | 7 | 11 | 10 | 13.5 |
| C | 5 | <5 | <5 | <5 | <5 | <5 | <5 | <5 | <5 | 11 | 16 | 26 | 19 |
| C | 6 | <5 | <5 | <5 | <5 | <5 | 5 | 7 | 8 | 8 | 8 | 26 | 26 |
| C | 7 | <5 | <5 | <5 | <5 | <5 | <5 | <5 | <5 | <5 | <5 | 6 | <5 |
| C | 8 | <5 | <5 | <5 | <5 | <5 | <5 | <5 | <5 | <5 | 7 | 12 | 13 |
| | Average | <5 | <5 | <5 | <5 | <5 | <5 | <5 | 5 | 7 | 8 | 17.5 | 15.2 |

EXAMPLE 5

Evaluation of Pour-On Formulations Containing 23-(O-Methyloxime)-LL-F28249α for Controlling Endoparasites in Infected Animals Evaluation of the pour-on formulations described in Example 2 above, i.e., Formulation 1 (Group B) and formulation 3 (Group C), for control of *Ostertagia ostertagi, Trichostrongylus axei,* and *Haemonchus placei* in the abomasum of the treated animals and *Cooperia punctata* and *Cooperia oncophora* adult worms in the small intestines of the treated animals is conducted using the procedures described below.

In these tests 6 calves per treatment are used. The calves are heavily infected with endoparasites and are randomly assigned to groups, each group having 3 males and 3 females. The calves are weighed and fecal egg counts made for each animal. Group 1 is then treated with the pour-on formulation B, i.e., the CRODAMOLS® formulation 1 from example 2 of the specification. Group 2 receive pour-on formulation C, formulation 3 from example 2.

Fourteen days after treatment the calves are necropsied and egg counts, larval counts and adult worm counts are made. These data are reported in Table 5 where it can be seen that the fecal egg count in treated calves 14 days after treatment is zero with both formulations, but in the untreated control there are about 183 eggs per calf. The data also show that the weight gains with treated calves is considerably better than the untreated controls. The data in Table 6 show that *Ostertagia ostertagi* is completely controlled with all treatments.

*Trichostrongylus axei* is controlled with the CRODAMOL®-INDOPOL® formulation C, but the CRODAMOL® formulation B in which INDOPOL® is omitted shows a break. With *Haemonchus placei* the CRODAMOL® formulation B and the CRODAMOL®-INDOPOL® formulation C give complete control of this larvae.

Finally, Table 7 shows complete control of *Cooperia punctata* with the CRODAMOL®-INDOPOL® formulation C, but breaks with CRODAMOL® alone, formulation B, in 3 out of 6 animals. Even more importantly, with *Cooperia oncophora* formulation B shows a break in 3 out of 6 animals; whereas, formulation C, CRODAMOL®-INDOPOL®, gives complete control of *Cooperia oncophora*.

TABLE 5

Fecal Egg Counts and Body Weights of Calves Used for Evaluation of Test Formulations For Control of Endoparasites in Infected Animals

| | | | Fecal Egg Count | | Calf Weights (lbs.) | |
|---|---|---|---|---|---|---|
| Formulation | Group | Sex | At Treatment | At Necropsy | | |
| B-<br>CRODAMOL®<br>Formula 1<br>from<br>Example 2 | 1 | F<br>F<br>F<br>M<br>M<br>M | 138<br>88<br>166<br>174<br>98<br>194 | 0<br>0<br>0<br>0<br>0<br>0 | 450<br>460<br>410<br>500<br>350<br>370 | 500<br>490<br>460<br>585<br>385<br>430 |
| | | | 858 | | 2,540 | 2,850 |
| C-<br>CRODAMOL®/<br>INDOPOL®<br>Formula 3<br>from<br>Example 2 | 2 | F<br>F<br>F<br>M<br>M<br>M | 98<br>220<br>118<br>292<br>512<br>406 | 0<br>0<br>0<br>0<br>0<br>0 | 400<br>490<br>435<br>225<br>470<br>410 | 450<br>550<br>480<br>270<br>520<br>465 |
| | | | 1,646 | | 2,430 | 2,735 |
| Untreated<br>Control | 3 | F<br>F<br>F<br>M<br>M<br>M | 104<br>170<br>172<br>304<br>182<br>166 | 222<br>366<br>334<br>266<br>146<br>196 | 475<br>385<br>440<br>380<br>425<br>400 | 265<br>325<br>510<br>440<br>495<br>480 |
| | | | 1,098 | 1,530 | 2,505 | 2,775 |

TABLE 6

Evaluation of Pour-On Formulations for Control of Endoparasite in the Abomasum of Treated Animals

| Formulation | Ostertagia Ostertagi | Tricho-strongylus Axei | Haemonchus Placei | Total Nematode Count |
|---|---|---|---|---|
| B<br>CRODAMOL® | —<br>—<br>—<br>—<br>— | —<br>—<br>—<br>—<br>8<br>— | —<br>—<br>—<br>—<br>—<br>— | —<br>—<br>—<br>—<br>8<br>— |
| C | — | — | — | — |

TABLE 6-continued

Evaluation of Pour-On Formulations for Control
of Endoparasite in the Abomasum of Treated Animals

| Formulation | Ostertagia Ostertagi | Tricho-strongylus Axei | Haemonchus Placei | Total Nematode Count |
|---|---|---|---|---|
| CRODAMOL ®/ | — | — | — | — |
| INDOPOL ® | — | — | — | — |
|  | — | — | — | — |
|  | — | — | — | — |
| Untreated | 6,460 | 7,390 | 130 | 14,030 |
| Control | 9,500 | 8,900 | 500 | 18,030 |
|  | 5,900 | 10,300 | 650 | 16,850 |
|  | 5,220 | 7,680 | 6 | 12,906 |
|  | 3,920 | 4,000 | 6 | 7,957 |
|  | 2,040 | 4,600 | — | 6,640 |
|  | 33,040 | 42,870 | 1,368 | 77,278 |

TABLE 7

Evaluation of Test Formulations for Control of
Endoparasites in the Small Intestine of Treated
Animals (Total Nematode Count)

| Formulation | Cooperia Punctata | Cooperia Oncophora |
|---|---|---|
| B | 24 | 36 |
| CRODAMOL ® | — | — |
|  | 33 | 33 |
|  | 240 | 184 |
|  | — | — |
|  | — | — |
|  | 297 | 253 |
| C | — | — |
| CRODAMOL ®/ | — | — |
| INDOPOL ® | — | — |
|  | — | — |
|  | — | — |
| Untreated | 2,880 | 4,560 |
| Control | 2,240 | 4,640 |
|  | 2,200 | 4,200 |
|  | 3,570 | 10,640 |
|  | 4,264 | 7,920 |
|  | 1,850 | 3,800 |
|  | 17,004 | 35,760 |

EXAMPLE 6

Evaluation of the Efficacy of Pour-On Formulations
Containing 23-(O-Methyloxime)-LL-F28249α
During Rainfall The objective of this study is to determine the potential effect of rainfall on the efficacy of a pour-on formulation of 23-(O-methyloxime)-LL-F28249α (0.5% w/v) against gastrointestinal nematodes. Formulation 10 reported in Example 2, above, is employed for the study.

Forty-eight mixed beef breed heifers are ranked according to the average of the day −3 and day −2 fecal nematode egg counts and randomly assigned to the following groups of 6 animals each:

Group I: Treatment with vehicle and no exposure to simulated rain (control);

Group II: Treatment with 23-(O-methyloxime)-LL-F28249α pour-on and no exposure to simulated rain;

Group III: Treatment with 23-(O-methyloxime)-LL-F28249α pour-on and exposure to simulated rain immediately prior to treatment;

Group IV: Treatment with 23-(O-methyloxime)-LL-F28249α pour-on and exposure to simulated rain 2 hours posttreatment;

Group V: Treatment with 23-(O-methyloxime)-LL-F28249α pour-on and exposure to simulated rain 6 hours posttreatment;

Group VI: Treatment with 23-(O-methyloxime)-LL-F28249α pour-on and exposure to simulated rain 24 hours posttreatment.

All cattle treated with 23-(O-methyloxime)-LL-F28249α pour-on are treated with 0.5 mg 23-(O-methyloxime)-LL-F28249α per kg of body weight. All animals exposed to simulated rain are sprayed with the equivalent of 1 inch of water for 30 minutes.

Following treatment, cattle are housed in outdoor pens which are partially covered by a three sided shed. Cattle remain outdoors during the entire posttreatment period. However, they are confined to a covered portion of the pen when it is raining or rainfall is imminent. This is done to prevent any confounding effect of natural rainfall on the interpretation of the results of this trial.

The simulated rainfall apparatus used in this trial consists of a 12 feet×12 feet pen with right angle directional spray nozzles in each corner. It is calculated that 89.75 gallons of water applied to this size pen are the equivalent of 1 inch of rain. This simulated rain is applied over a 30 minute period which is equivalent to 2 inches of rain per hour. According to the U.S. Department of Interior Geological Survey (The National Atlas of the United States of America, p. 97, Washington, D.C., 1970), 2 inches of rain per hour is the mean annual maximum hourly rainfall in the United States. The actual volumes of water applied to each of the treatment groups exposed to simulated rain are 101.3, 91, 91.4 and 91.4 for treatment Groups III, IV, V and VI, respectively.

Fecal samples are taken from all animals on days 7, 14 and 21 posttreatment to evaluate nematode egg counts. The results of this study are summarized in Table 8 below. The values are expressed as number of eggs per 1 g of feces.

TABLE 8

THE INFLUENCE OF SIMULATED RAIN
ON THE EFFICACY OF 0.5% W/V POUR-ON OF
23-(O-METHYLOXIME)-LL-F28249α IN
THE REDUCTION OF NEMATODE
EGG OUTPUT IN FECES IN CATTLE

| Group | Geometric Means | | | % Reduction | | |
|---|---|---|---|---|---|---|
|  | Day 7 | Day 14 | Day 21 | Day 7 | Day 14 | Day 21 |
| I | 97$^a$ | 44$^a$ | 82$^a$ |  |  |  |
| II | <1$^b$ | <1$^c$ | <1$^c$ | >99.9 | >99.9 | 99.8 |
| III | <1$^b$ | <1$^{bc}$ | <1$^{bc}$ | 99.8 | 98.9 | 98.7 |
| IV | <1$^b$ | <1$^c$ | <1$^{bc}$ | 99.7 | 99.7 | 99.2 |
| V | 1$^b$ | 2$^b$ | 4$^b$ | 98.9 | 94.5 | 94.5 |
| VI | <1$^b$ | <1$^c$ | <1$^c$ | 99.9 | 99.7 | 99.4 |

$^{a,b,c}$Means in the same column with different superscripts differ at P < 0.05.

Treatment with 23-(O-methyloxime)-LL-F28249α significantly reduces nematode egg counts at all times posttreatment regardless of exposure to simulated rainfall. Treatment with 23-(O-methyloxime)-LL-F28249α pour-on without the influence of simulated rain (Group II) is greater than 99.8% effective in reducing fecal output of nematode eggs at all 3 posttreatment sampling times. At day 7 posttreatment, there is no effect of simulated rain either pre- (Group III) or posttreatment (Group IV, V and VI) on the reduction of fecal nematode egg output. At days 14 and 21 posttreatment, simulated rainfall prior to treatment (Group III) and at 2 (Group IV) and 24 hours posttreatment (Group VI) has no effect on the reduction of fecal nematode egg output as compared with the positive controls (Group II). At days 14 and 21 posttreatment, simulated rain at 6 hours posttreatment (Group V) results in a significant reduction in fecal nematode egg output as compared to the untreated controls (Group I).

On day 21 posttreatment, fecal samples from the eight control animals are analyzed. The results indicate that the infections include the following genera: Cooperia, Haemonchus, Ostertagia and Trichostrongylus. No adverse effects of 23-(O-methyloxime)-LL-F28249α pour-on are observed on overall animal health at 1, 2, 3, 4, 7 and 14 days posttreatment. Animals are examined at the same posttreatment times for skin reactions at the pour-on site and no reactions are observed.

This study demonstrates that simulated rainfall has little, if any, effect on the efficacy of 23-(O-methyloxime)-LL-F28249α pour-on.

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

We claim:

1. A non-aqueous pour-on, water-fast composition for combatting helminth, acarid or arthropod endo- or ectoparasitic insect infestation or infection of a mammalian quadruped comprising an anthelmintically, acaricidally or an arthropod endo- or ectoparasiticidally effective amount of a compound selected from the group consisting of LL-F28249α-λ, a 23-oxo or 23-imino derivative of LL-F28249α-λ, dissolved or dispersed in a mixture comprising: from about 5.0% to about 20% w/v of an aromatic solvent having a mixed aniline point of from about 13.4° C. to about 15.4° C., a Kauri-butanol value between about 90 to about 96 and a specific gravity @ 15.6°/15.6° C. of from about 0.872 to about 0.985; from about 1.0% w/v to about 15.0% w/v of PPG-2 myristyl ether propionate; from about 1.0% w/v to about 15.0% w/v of a polybutene having a number average molecular weight of from 320 to 3000 and a Cleveland open cup flash point of from 154° C. to 307° C.; from 0 to about 2.0% w/v of a dye, an antimicrobial agent, an antioxidant or a mixture thereof; and sufficient quantity of a pharmacologically acceptable oil to total 100% w/v.

2. The composition according to claim 1, wherein the compound is 23-(O-methyloxime)-LL-F28249α.

3. The composition according to claim 1, wherein the compound is LL-F28249α.

4. The composition according to claim 1, comprising from about 0.1% w/v to about 5.0% w/v of 23-(O-methyloxime)-LL-F 28249α; about 5.0% w/v to about 20% w/v of the aromatic solvent; about 1.0% w/v to about 15.0% w/v of PPG-2 myristyl ether propionate; about 1.0% w/v to about 15.0% w/v of polybutene; from 0 to about 2.0% w/v of a dye, an antimicrobial agent, an antioxidant or a mixture thereof; and sufficient quantity of a mineral oil or a vegetable oil to total 100% w/v.

5. A method for treating helminth, acarid or arthropod endo- or ectoparasitic insect infection or infestation in a mammalian quadruped which comprises pouring onto the skin or hide of the quadruped to be treated an anthelmintically, acaricidally or arthropod endo- or ectoparasiticidally effective amount of a composition of claim 1.

6. The method according to claim 5, wherein the quadruped is selected from the group consisting of a cow, a sheep, a deer, a horse, a swine, a goat, a dog and a cat.

7. The method according to claim 5, wherein the composition poured on the skin or hide of the quadruped comprises about 0.1% w/v to 5.0% w/v of 23-(O-methyloxime)-LL-F 28249α; about 5.0% w/v to 20% w/v of the aromatic solvent; about 1.0% w/v to about 15.0% w/v of PPG-2 myristyl ether propionate; about 1.0% w/v to about 15.0% w/v of polybutene; from 0 to about 2.0% w/v of a dye, an antimicrobial agent, an antioxidant or a mixture thereof; and sufficient quantity of a mineral oil or a vegetable oil to total 100% w/v.

8. The method according to claim 5, wherein the pour-on composition is applied to the quadruped in sufficient amount to provide about 0.2 mg/kg to about 1.0 mg/kg of body weight of the compound.

9. The method according to claim 8, wherein the compound is 23-(O-methyloxime)-LL-F28249α.

10. The method according to claim 5, which comprises pouring the composition onto wet skin or hide.

11. A method for treating or controlling psoroptic, chorioptic, sarcoptic or demodectic mange on a mammalian quadruped which comprises pouring onto the skin or hide of the quadruped a non-aqueous pour-on composition of claim 1 containing a sufficient amount of the compound 23-(O-methyloxime)-LL-F28249α to provide about 0.1 mg/kg to about 5.0 mg/kg of body weight of said compound.

12. The method according to claim 11, wherein the quadruped is selected from the group consisting of a cow, a sheep, a deer, a horse, a swine, a goat, a dog and a cat.

13. The method according to claim 11, which comprises pouring the composition onto wet skin or hide.

* * * * *